(12) United States Patent
Cho (10) Patent No.: US 9,168,109 B2
(45) Date of Patent: Oct. 27, 2015

(54) MOLD FOR DENTAL COPINGS AND COPINGS PRODUCED BY USING THE MOLD

(71) Applicant: Sang Choon Cho, New York, NY (US)

(72) Inventor: Sang Choon Cho, New York, NY (US)

(73) Assignee: EBI CO., LTD. (KR)

( * ) Notice: Subject to any disclaimer, the term of this patent is extended or adjusted under 35 U.S.C. 154(b) by 0 days.

(21) Appl. No.: 13/891,552

(22) Filed: May 10, 2013

(65) Prior Publication Data

US 2013/0244207 A1    Sep. 19, 2013

Related U.S. Application Data

(63) Continuation of application No. PCT/KR2011/006383, filed on Aug. 30, 2011.

(30) Foreign Application Priority Data

Nov. 12, 2010    (KR) .................. 10-2010-0113003

(51) Int. Cl.
*A61C 8/00* (2006.01)
*A61C 9/00* (2006.01)

(52) U.S. Cl.
CPC ............... *A61C 8/0001* (2013.01); *A61C 8/005* (2013.01); *A61C 9/00* (2013.01)

(58) Field of Classification Search
CPC ........ B29D 1/00; A61C 8/0001; A61C 8/005; B29C 45/2618; B29C 45/262; B29C 45/2622
USPC ............. 425/2, 175, 176, 179, 180, 418, 423, 425/438; 249/54, 59, 63, 181; 433/34, 42, 433/45–47, 161; 264/16–19
See application file for complete search history.

(56) References Cited

U.S. PATENT DOCUMENTS

| 1,227,680 A | * | 5/1917 | Segre ............................ 264/318 |
| 2,100,985 A | * | 11/1937 | Smally .......................... 425/125 |
| 3,150,222 A | * | 9/1964 | Blanstein et al. ............. 264/318 |

(Continued)

FOREIGN PATENT DOCUMENTS

| JP | H10118097 A | 5/1998 |
| JP | 2000506037 A | 5/2000 |

(Continued)

OTHER PUBLICATIONS

International Search Report Application No. PCT/KR2011/006383 Completed: Apr. 20, 2012; Mailing Date: Apr. 20, 2012 2 pages.

(Continued)

*Primary Examiner* — James Sanders
(74) *Attorney, Agent, or Firm* — St. Onge Steward Johnston & Reens LLC (57) ABSTRACT

A mold for producing a coping used in a dental implant includes a male component having a protrusion and a female screw forming part. The mold further includes a female component having a recess and a male screw forming part having a different rotation direction from that of the female screw forming part. A cavity for producing the coping is formed by combining the male and female components. Since the mold includes a male component having a female screw forming part, and a female component having a male screw forming part with a different rotation direction than the female screw forming part, a produced coping may be easily separated from the male and female components.

2 Claims, 7 Drawing Sheets

(56) References Cited

U.S. PATENT DOCUMENTS

| | | | |
|---|---|---|---|
| 3,216,607 A * | 11/1965 | Capucio | 220/288 |
| 3,730,664 A * | 5/1973 | Hultgren | 425/338 |
| 4,162,625 A * | 7/1979 | Simmons | 72/54 |
| 4,380,299 A * | 4/1983 | Alejandro Llera | 215/252 |
| 4,575,340 A | 3/1986 | Lustig | |
| 4,617,159 A * | 10/1986 | Miller | 264/16 |
| 4,787,596 A * | 11/1988 | Folding et al. | 249/59 |
| 5,223,158 A * | 6/1993 | Lizenby | 249/59 |
| 5,342,201 A * | 8/1994 | Oden | 433/223 |
| 5,437,551 A * | 8/1995 | Chalifoux | 433/173 |
| 5,490,810 A * | 2/1996 | Hahn et al. | 451/165 |
| 5,873,721 A * | 2/1999 | Willoughby | 433/173 |
| 6,126,445 A * | 10/2000 | Willoughby | 433/223 |
| 6,257,891 B1 * | 7/2001 | Moore et al. | 433/218 |
| 6,426,030 B1 * | 7/2002 | Julian | 264/318 |
| 6,609,694 B2 * | 8/2003 | Francois et al. | 249/59 |
| 6,623,265 B1 * | 9/2003 | Day | 425/438 |
| 6,848,898 B2 | 2/2005 | Shoher et al. | |
| 7,232,301 B2 * | 6/2007 | Avalle | 425/110 |
| 2002/0027121 A1 * | 3/2002 | McNary et al. | 215/252 |
| 2003/0036035 A1 * | 2/2003 | Chen | 433/172 |
| 2004/0004302 A1 | 1/2004 | Shoher et al. | |
| 2012/0193823 A1 * | 8/2012 | Goetzinger et al. | 264/16 |
| 2012/0301849 A1 * | 11/2012 | Wang et al. | 433/174 |

FOREIGN PATENT DOCUMENTS

| | | | | |
|---|---|---|---|---|
| JP | 3312525 B2 * | 8/2002 | | B29C 45/44 |
| KR | 100562356 B1 | 3/2006 | | |
| WO | 9731585 A1 | 9/1997 | | |
| WO | WO 0030831 A1 * | 6/2000 | | B29C 45/43 |
| WO | WO 2009074217 A2 * | 6/2009 | | B29C 45/26 |

OTHER PUBLICATIONS

Translation of a Notice of Allowance from the Korean Intellectual Property Office Application No. 10-2011-0069473 Issued: Jun. 13, 2012 1 page.

* cited by examiner

MOLD FOR DENTAL COPINGS AND COPINGS PRODUCED BY USING THE MOLD

FIELD OF THE INVENTION

The present invention relates to a mold for dental copings and copings produced by using the mold, and more particularly, to a mold for dental copings to easily separate a produced coping from male and female molds, and copings produced by using the mold.

BACKGROUND OF THE INVENTION

Figure 1:
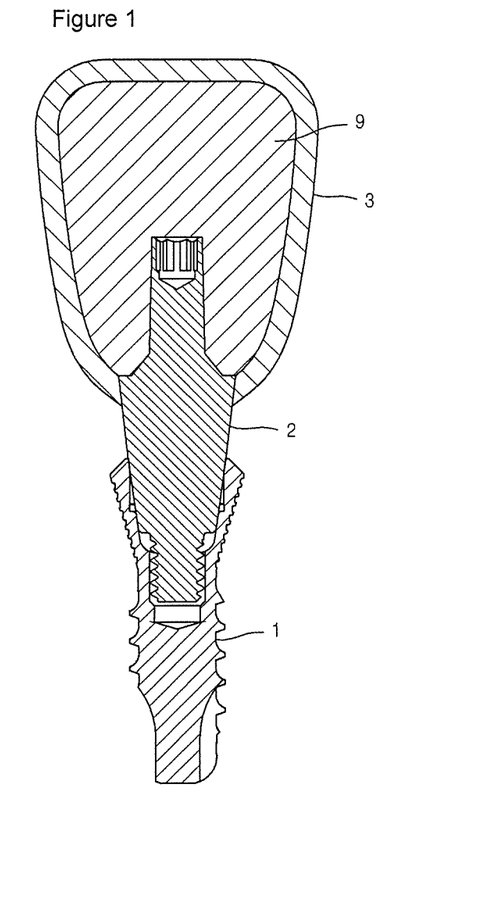
FIG. 1 is a cross-sectional diagram for describing a conventional temporary crown bonding method.
Figure 2:
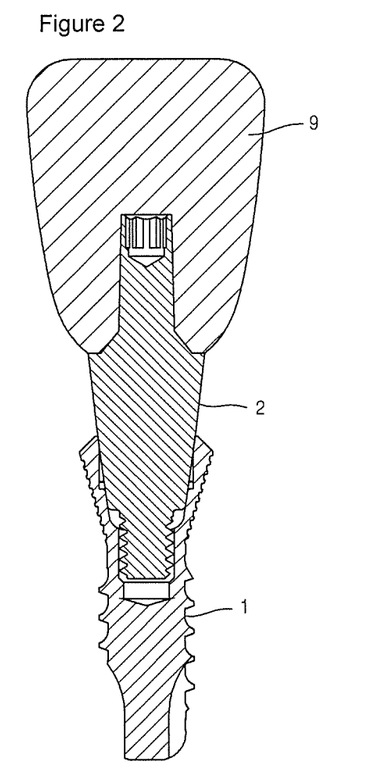
FIG. 2 is a cross-sectional diagram showing a dental implant after a crown mold illustrated in FIG. 1 is removed.

When a dental implant surgery is performed, for the patient's convenience, a temporary crown is bonded to a dental implant implanted into the alveolar bone. FIG. 2 shows an exemplary case when a temporary crown 9 is mounted. In order to mount the temporary crown 9, a temporary abutment 2 is combined with an upper portion of a dental implant 1 implanted into the alveolar bone. Then, as illustrated in FIG. 1, acrylic resin is filled in a crown mold 3 for forming the temporary crown 9, the crown mold 3 is fixed to the temporary abutment 2 until the acrylic resin is cured, thereby forming the temporary crown 9.

However, in the above conventional temporary crown bonding method, a large amount of heat is generated and the generated heat lasts for a long time during curing of the acrylic resin filled in the crown mold 3.

In particular, considering that the acrylic resin filled in the crown mold 3 is cured in the mouth of a patient, the patient may experience inconvenience due to the generated heat, and the inconvenience may increase if the generated heat lasts for a long time.

Also, since the conventional temporary crown bonding method directly cures the acrylic resin filled in the crown mold 3, it is not easy to precisely bond the temporary crown 9 to the temporary abutment 2 at a desired position and angle.

SUMMARY OF THE INVENTION

The present invention provides a mold for dental copings to easily separate a produced coping from male and female molds.

The present invention provides copings produced by using the mold.

According to the present invention, since a mold includes a male mold including a female screw forming part formed on an end portion of a protrusion, and a female mold including a male screw forming part formed on an inner circumferential surface of a recess and having a different rotation direction from that of the female screw forming part, a produced coping may be easily separated from the male and female molds. Also, since the mold produces the coping by using existing materials and tools generally used in dental offices, in comparison to conventional plastic copings purchased from implant companies at high prices, an overall cost may be reduced.

DETAILED DESCRIPTION OF THE INVENTION

According to an aspect of the present invention, there is provided a mold for producing a coping used in a dental implant, the mold including a male mold comprising a protrusion for forming an inner circumferential surface of the coping, and a female screw forming part formed on an end portion of the protrusion; and a female mold comprising a recess for forming an outer circumferential surface of the coping, and a male screw forming part formed on an inner circumferential surface of the recess and having a different rotation direction from that of the female screw forming part, wherein a cavity for producing the coping is formed by combining the male and female molds.

The male and female molds may be integrally formed as one member.

According to another aspect of the present invention, there is provided a coping produced by using the mold.

The coping may be used to combine a dental implant and a temporary crown, and may be formed of the same material as the temporary crown.

Hereinafter, the present invention will be described in detail by explaining embodiments of the invention with reference to the attached drawings.

Figure 3:
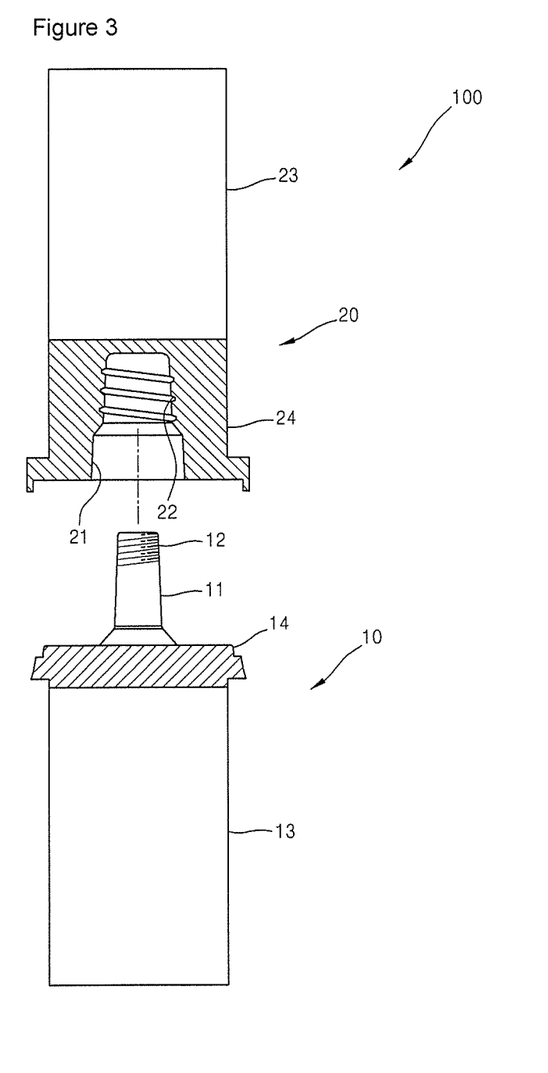
FIG. 3 is a cross-sectional view of a mold for dental copings, according to an embodiment of the present invention.
Figure 4:
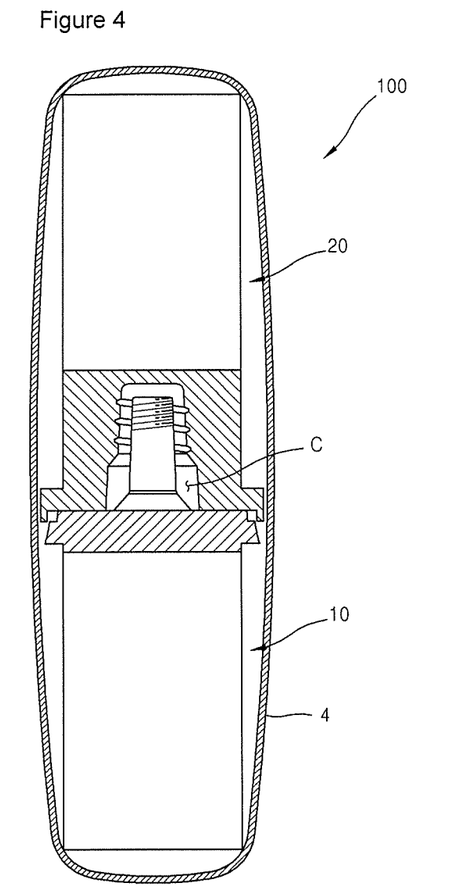
FIG. 4 is a cross-sectional diagram showing male and female molds illustrated in FIG. 3.
Figure 5:
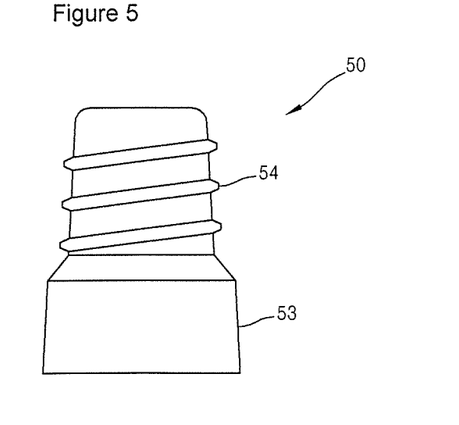
FIG. 5 is a front view of a coping produced by using the male and female molds illustrated in FIG. 3.

FIG. 3 is a cross-sectional view of a mold 100 for dental copings, according to an embodiment of the present invention. FIG. 4 is a cross-sectional diagram showing male and female molds 10 and 20 illustrated in FIG. 3. FIG. 5 is a front view of a coping produced by using the male and female molds 10 and 20 illustrated in FIG. 3.

Referring to FIGS. 3 through 5, the mold 100 is used to produce a coping 50 for a dental implant 1 (see FIG. 7) and includes the male and female molds 10 and 20.

The male mold 10 is used to form a cavity C for producing the coping 50, and includes a protrusion 11, a female screw forming part 12, and a handle 13.

The protrusion 11 has a truncated cone shape protruding from one surface of a male body 14 having a circular plate shape, and is used to form an inner circumferential surface 51 of the coping 50 to be produced.

The female screw forming part 12 is a left-handed screw part formed on an outer circumferential surface of an end portion of the protrusion 11, and is used to form a female screw 52 formed on the inner circumferential surface 51 of the coping 50 to be produced.

The handle 13 is a bar-shaped member, and is combined with another surface of the male body 14.

The female mold 20 is combined with the male mold 10 to form the cavity C for producing the coping 50, and includes a recess 21, a male screw forming part 22, and a handle 23.

The recess 21 is recessed in a circular hole shape in one surface of a female body 24 having a cylinder shape, and is used to form an outer circumferential surface 53 of the coping 50 to be produced.

The male screw forming part 22 is a right-handed screw part formed on an inner circumferential surface of the recess 21, and is used to form a male screw 54 formed on the outer circumferential surface 53 of the coping 50 to be produced. Accordingly, the male screw forming part 22 and the female screw forming part 12 are screw parts having opposite rotation directions.

The handle 23 is a bar-shaped member, and is combined with another surface of the female body 24.

Accordingly, if the protrusion 11 of the male mold 10 and the recess 21 of the female mold 20 are combined as illustrated in FIG. 4, the cavity C for producing the coping 50 may be formed.

An example of a method using the mold 100 will now be described.

Initially, the male and female molds 10 and 20 are individually disposed in such a way that the handles 13 and 23 contact the ground and the protrusion 11 and the recess 21 face upward. The protrusion 11 and the recess 21 are cleaned by using compression air to remove foreign substances.

Silicon spray is applied as a mold releasing to the cleaned protrusion 11 and the recess 21, and is dried. After the silicon spray is dried, a small amount of acrylic resin powder is put as a main material on a mixing slab, and a liquid-type curing agent to chemically react with the powder is added while mixing the powder and the curing agent uniformly by using a spatula.

After the powder and the curing agent are uniformly mixed into a dough, the dough is carefully injected into the recess 21 of the female mold 20 by using a 1 cc syringe having no needle tip. In this case, the injection amount of the dough has to be appropriately controlled to prevent the dough from running over into the recess 21.

Then, after the protrusion 11 of the male mold 10 is fitted into the recess 21 of the female mold 20, as illustrated in FIG. 4, the male and female molds 10 and 20 are firmly combined by using a polyamide band referred to as a kapton band 4.

After it is confirmed that the male and female molds 10 and 20 are firmly combined, the combined male and female molds 10 and 20 are put into hot water and are kept for about 3 to 5 minutes, and the acrylic resin having a self-curing property is cured, thereby curing the coping 50.

After the coping 50 is completely cured, the combined male and female molds 10 and 20 are taken out of the hot water, and the kapton band 4 is removed.

By respectively holding the handles 13 and 23 of the male and female molds 10 and 20 and rotating the handle 23 of the female mold 20 in a counterclockwise direction with respect to the handles 13 of the male mold 10, the coping 50 is separated from the recess 21 of the female mold 20 while being bonded to the protrusion 11 of the male mold 10.

After the male and female molds 10 and 20 are separated as described above, redundant resin around the coping 50 bonded to the protrusion 11 of the male mold 10 is removed. By respectively holding the handle 13 of the male mold 10 and the coping 50 and rotating the coping 50 in a clockwise direction with respect to the handle 13 of the male mold 10, the coping 50 is separated from the protrusion 11 of the male mold 10, thereby completely producing the coping 50 as illustrated in FIGS. 5 and 6.

Figure 6:
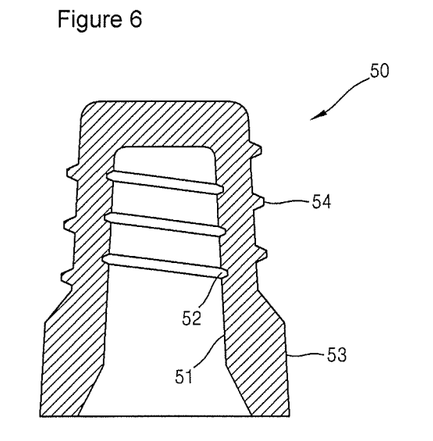
FIG. 6 is a cross-sectional view of the coping illustrated in FIG. 5.

As illustrated in FIG. 6, the coping 50 is a cork-shaped member having an open bottom. The female screw 52 that is a left-handed screw is formed on the inner circumferential surface 51 of the coping 50, and the male screw 54 that is a right-handed screw is formed on the outer circumferential surface 53 of the coping 50.

Figure 7:
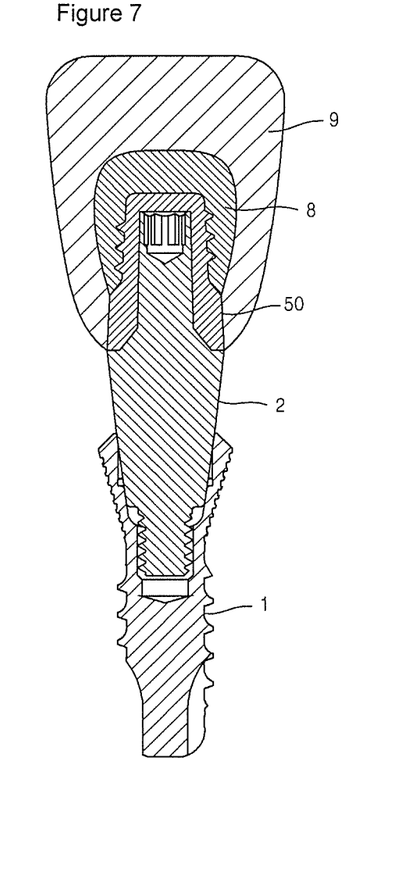
FIG. 7 is a cross-sectional diagram showing a temporary crown bonded to the coping illustrated in FIG. 5.

Meanwhile, the produced coping 50 may be used to combine the dental implant 1 and a temporary crown 9 as illustrated in FIG. 7. An example of a method of using the coping 50 will now be described. Initially, a temporary abutment 2 is combined with an upper portion of the dental implant 1 implanted into the alveolar bone, the coping 50 is tight-fitted onto an end portion of the temporary abutment 2, a small amount of an adhesive 8 formed of the same acrylic resin used to form the coping 50 is spread on an end portion of the coping 50, and then the temporary crown 9 formed of the same acrylic resin as the coping 50 is put on the adhesive 8 and is kept until the adhesive 8 is cured, thereby completely mounting the temporary crown 9. In this case, if necessary, in order to accurately mount the temporary crown 9, the temporary crown 9 may be repeatedly mounted and separated by checking an occlusal status after mounting the temporary crown 9.

Since the above mold 100 includes the male mold 10 including the female screw forming part 12 formed on the end portion of the protrusion 11, and the female mold 20 including the male screw forming part 22 formed on the inner circumferential surface of the recess 21 and having a different rotation direction from that of the female screw forming part 12, the produced coping 50 may be easily separated from the male and female molds 10 and 20.

Also, since the mold 100 produces the coping 50 by using existing materials (acrylic resin powder, etc.) and tools (a mixing slab, a mixing spatula, etc.) generally used in dental offices, in comparison to conventional plastic copings purchased from implant companies at high prices, a cost for the coping 50 may be reduced.

Meanwhile, since the coping 50 produced by using the mold 100 is formed of the same acrylic resin as the adhesive 8 and the temporary crown 9, a bonding force between the coping 50 and the temporary crown 9 may be excellent.

Also, if the temporary crown 9 is bonded by using the coping 50 in the mouth of a patient, in comparison to a conventional temporary crown bonding method for curing a large amount of acrylic resin filled in the crown mold 3, since only a small mount of the adhesive 8 is cured in the mouth of the patient, a small amount of heat is generated and the generated heat lasts for a short time during bonding of the temporary crown 9. Accordingly, the patient may not experience inconvenience in relation to heat.

Furthermore, if the temporary crown 9 is bonded by using the coping 50 in the mouth of a patient, unlike the conventional temporary crown bonding method for directly curing acrylic resin filled in the crown mold 3, since the temporary crown 9 is bonded by using the coping 50, the temporary crown 9 may be precisely bonded in a desired position and angle.

Figure 8:
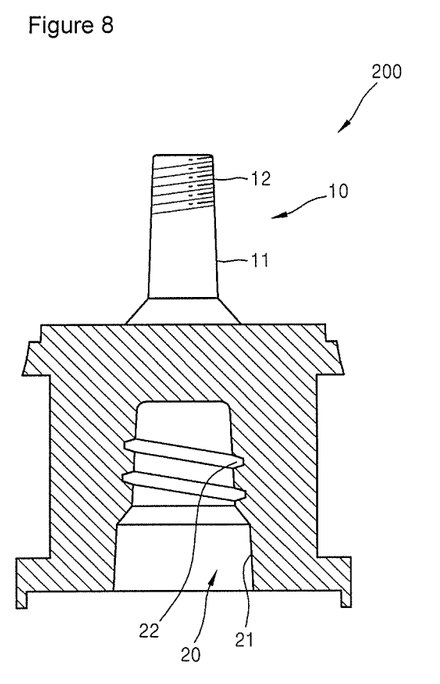
FIG. 8 is a cross-sectional view of a mold for dental copings, according to another embodiment of the present invention.

FIG. 8 is a cross-sectional view of a mold 200 for dental copings, according to another embodiment of the present invention. The mold 200 has the same structure and function as those of the mold 100 illustrated in FIG. 3 except that the male and female molds 10 and 20 are aligned on the same axis and are integrally formed respectively on upper and lower surfaces of one member, and thus, detailed descriptions thereof will not be provided here.

Figure 9:
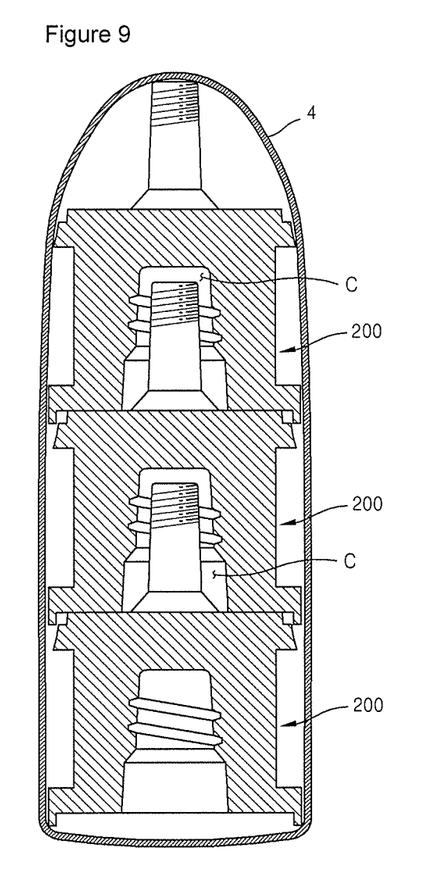
FIG. 9 is a cross-sectional view showing use of the mold illustrated in FIG. 8.

As illustrated in FIG. 9, if a plurality of molds 200 are connected in a line such that the male mold 10 is inserted into the female mold 20, a plurality of copings 50 may be produced by performing a curing process once. For example, if three molds 200 are used, two copings 50 may be produced at once.

Although the mold 100 or 200 for producing the coping 50 in which the right-handed screw 54 is formed on the outer circumferential surface 53 and the left-handed screw 52 is formed on the inner circumferential surface 51 is described in the above embodiments, a mold for producing a coping in which a left-handed screw is formed on an outer circumferential surface and a right-handed screw is formed on an inner circumferential surface may also be produced.

When the mold 100 or 200 is used to produce the coping 50 for combining the dental implant 1 and the temporary crown 9 in the above embodiments, an impression coping may be produced, and since pattern resin such as acrylic resin may be used, a casting coping may also be produced.

While the present invention has been particularly shown and described with reference to exemplary embodiments thereof, it will be understood by one of ordinary skill in the art that various changes in form and details may be made therein without departing from the spirit and scope of the invention as defined by the following claims and their equivalents.

What is claimed is:

1. A mold for producing a coping used in a dental implant, the mold comprising:
    a male mold comprising a protrusion for forming an inner circumferential surface of the coping, and a female screw forming part formed on an end portion of the protrusion; and
    a female mold comprising a recess for forming an outer circumferential surface of the coping, and a male screw forming part formed on an inner circumferential surface of the recess and having a different rotation direction from that of the female screw forming part,
    wherein a cavity for producing the coping is formed by combining the male and female molds.

2. The mold of claim 1, wherein the male and female molds are integrally formed as one member.

* * * * *